(12) United States Patent
Nappa

(10) Patent No.: US 8,143,462 B2
(45) Date of Patent: Mar. 27, 2012

(54) PROCESSES FOR THE SYNTHESIS OF 2-CHLORO-1,1,1,3,3,4,4,4-HEPTAFLUORO-2-BUTENE AND HEXAFLUORO-2-BUTYNE

(75) Inventor: Mario Joseph Nappa, Newark, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 494 days.

(21) Appl. No.: 12/334,873

(22) Filed: Dec. 15, 2008

(65) Prior Publication Data

US 2009/0156869 A1   Jun. 18, 2009

Related U.S. Application Data

(60) Provisional application No. 61/014,270, filed on Dec. 17, 2007.

(51) Int. Cl.
*C07C 17/25* (2006.01)
(52) U.S. Cl. ...................................... 570/156
(58) Field of Classification Search .................. None
See application file for complete search history.

(56) References Cited

U.S. PATENT DOCUMENTS

| | | | |
|---|---|---|---|
| 2,885,449 A | 5/1959 | Stahl et al. | |
| 2,900,423 A | 8/1959 | Smith | |
| 3,192,274 A * | 6/1965 | Baranauckas et al. | 570/156 |
| 5,157,171 A | 10/1992 | Sievert et al. | |
| 5,162,594 A | 11/1992 | Krespan | |
| 5,243,103 A | 9/1993 | Lerot et al. | |
| 6,066,768 A * | 5/2000 | Nappa et al. | 570/134 |
| 6,540,933 B1 | 4/2003 | Sievert | |
| 2002/0035300 A1* | 3/2002 | Rao et al. | 570/156 |
| 2008/0269532 A1 | 10/2008 | Swearingen | |

FOREIGN PATENT DOCUMENTS

WO   WO9516656   6/1995

OTHER PUBLICATIONS

Henne et al (J.Am.Chem.Soc., 1949, 71, 298-300).*
Runge et al (Tetrahedron Letters (1990), 31(38), 5453-6).*
Okano et al (Journal of Fluorine Chemistry (1988), 38(2).*
CRC Handbook of Chemistry and Physics, 81st Edition, (2000-2001) (Book Not Included).
Journal of Fluorine Chemistry, vol. 89, No. 1, pp. 125-130, Viacheslav A. Petrov, Garl G. Krespan and Bruce E. Smart, (Elsevier Science, BV, 1998).
Heterogeneous Catalysis in Industrial Practice, 2nd Edition (McGraw-Hill, New York, 1991) (Book Not Included).
Journal of Cataysis, vol. 81, pp. 204-213, E. Iglesia~ and M. Boudart, (Elsevier Science, USA, 1983).
Burger H., et al, Vibrational Spectra and Normal Coordinate Analysis of CF3 Compounds, Journal of Molecular Structure, vol. 84, 1982, pp. 49-68.

* cited by examiner

*Primary Examiner* — Sudhakar Katakam

(57) ABSTRACT

Disclosed is a process comprising reacting $CF_3CCl_2CF_2CF_3$ (CFC-318ma) with hydrogen in the presence of a dehalogenation catalyst to produce $CF_3CCl=CFCF_3$ (CFC-1317mx). Also disclosed is a process comprising reacting $CF_3CCl=CFCF_3$ (CFC-1317mx) with hydrogen in the presence of a dehalogenation catalyst to produce $CF_3C\equiv CCF_3$ (hexafluoro-2-butyne). Hexafluoro-2-butyne can be used to produce $CF_3CH=CHCF_2CF_3$ (1,1,1,4,4,5,5,5-octafluoro-2-pentene).

9 Claims, No Drawings

US 8,143,462 B2

PROCESSES FOR THE SYNTHESIS OF 2-CHLORO-1,1,1,3,3,4,4,4-HEPTAFLUORO-2-BUTENE AND HEXAFLUORO-2-BUTYNE

CROSS REFERENCE(S) TO RELATED APPLICATION(S)

This application claims the priority benefit of U.S. Provisional Patent Application No. 61/014,270, filed Dec. 17, 2007.

BACKGROUND

1. Field of the Disclosure

This present invention relates to processes for synthesizing fluorocarbons. In particular, the processes are for synthesizing 2-chloro-1,1,1,3,3,4,4,4-heptafluoro-2-butene and hexafluoro-2-butyne.

2. Description of the Related Art

The fluorocarbon industry has been working for the past few decades to find replacement refrigerants for the ozone depleting chlorofluorocarbons (CFC's) and hydrochlorofluorocarbons (HCFC's) that are being phased out as a result of the Montreal Protocol. The solution for many applications has been the commercialization of hydrofluorocarbon (HFC) compounds for use as refrigerants, solvents, fire extinguishing agents, blowing agents and propellants. These new compounds, such as HFC refrigerants, HFC-134a being the most widely used at this time, have zero ozone depletion potential and thus are not affected by the current regulatory phase-out as a result of the Montreal Protocol.

In addition to ozone depleting concerns, global warming is another environmental concern in many of these applications. Thus, there is a need for compositions that meet both low ozone depletion standards as well having low global warming potentials. Certain hydrofluoroolefins are believed to meet both goals. There is a need for manufacturing processes that provide halogenated hydrocarbons and fluoroolefins that contain no chlorine that also have a low global warming potential.

SUMMARY OF THE INVENTION

The present disclosure provides a process comprising reacting $CF_3CCl_2CF_2CF_3$ (CFC-318ma) with hydrogen in the presence of a dehalogenation catalyst to produce $CF_3CCl\!=\!CFCF_3$ (CFC-1317mx).

The present disclosure also provides a process comprising reacting $CF_3CCl\!=\!CFCF_3$ (CFC-1317mx) with hydrogen in the presence of a dehalogenation catalyst to produce $CF_3C\!\equiv\!CCF_3$ (hexafluoro-2-butyne).

DETAILED DESCRIPTION OF THE PREFERRED EMBODIMENTS

Many aspects and embodiments have been described above and are merely exemplary and not limiting. After reading this specification, skilled artisans appreciate that other aspects and embodiments are possible without departing from the scope of the invention. Other features and benefits of any one or more of the embodiments will be apparent from the following detailed description, and from the claims.

Before addressing details of embodiments described below, some terms are defined or clarified.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, use of "a" or "an" are employed to describe elements and components described herein. This is done merely for convenience and to give a general sense of the scope of the invention. This description should be read to include one or at least one and the singular also includes the plural unless it is obvious that it is meant otherwise.

Group numbers corresponding to columns within the Periodic Table of the elements use the "New Notation" convention as seen in the *CRC Handbook of Chemistry and Physics*, 81$^{st}$ Edition (2000-2001).

Unless otherwise defined, all technical and scientific terms used herein have the same meaning as commonly understood by one of ordinary skill in the art to which this invention belongs. Although methods and materials similar or equivalent to those described herein can be used in the practice or testing of embodiments of the present invention, suitable methods and materials are described below. All publications, patent applications, patents, and other references mentioned herein are incorporated by reference in their entirety, unless a particular passage is cited. In case of conflict, the present specification, including definitions, will control. In addition, the materials, methods, and examples are illustrative only and not intended to be limiting.

As used herein, a reaction zone may be a reaction vessel fabricated from nickel, iron, titanium or their alloys, as described in U.S. Pat. No. 6,540,933. A reaction vessel of these materials (e.g., a metal tube) may also be used. When reference is made to alloys, it is meant a nickel alloy containing from about 1 to about 99.9 weight percent nickel, an iron alloy containing about 0.2 to about 99.8 weight percent iron, and a titanium alloy containing about 72 to about 99.8 weight percent titanium. Of note is the use of a tube such as above, packed with a catalyst, wherein the tube is made of nickel or alloys of nickel such as those containing about 40 weight percent to about 80 weight percent nickel, e.g., Inconel™ 600 nickel alloy, Hastelloy™ C617 nickel alloy or Hastelloy™ C276 nickel alloy.

The present invention is directed to two processes, one for making CFC-1317mx (2-chloro-1,1,1,3,3,4,4,4-heptafluoro-2-butene, $CF_3CF\!=\!CClCF_3$), and the other for making hexafluoro-2-butyne ($CF_3C\!\equiv\!CCF_3$). These compounds, in addition to CFC-318ma ($CF_3CF_2CCl_2CF_3$), may be used as intermediates to make 1,1,1,4,4,4-hexafluoro-2-butene. In addition, hexafluoro-2-butyne can be used to produce $CF_3CH\!=\!CHCF_3$ (1,1,1,4,4,4-hexafluoro-2-butene).

Thus according to one aspect of the present invention, a process is provided for the synthesis of CFC-1317mx comprising reacting $CF_3CCl_2CF_2CF_3$ (CFC-318ma) with hydrogen in the presence of a dehalogenation catalyst, thus producing $CF_3CCl\!=\!CFCF_3$ (CFC-1317mx).

In one embodiment, the CFC-318ma may be produced by any method known in the art.

In one embodiment, the CFC-318ma may be produced by an addition reaction of CFC-114a ($CF_3CCl_2F$, 1,1-dichloro-1,2,2,2-tetrafluoroethane) and TFE ($CF_2\!=\!CF_2$, tetrafluoroethylene) in the presence of a catalyst. In one embodiment, the catalyst for the addition reaction comprises an aluminum halide catalyst. The aluminum halide catalyst composition may have a bulk formula of $AlCl_xBr_yF_{3-x-y}$ wherein the average value of x is 0 to 3, the average value of y is 0 to 3-x, provided that the average values of x and y are not both 0. In another embodiment, x is from about 0.10 to 3.00 and y is 0. Aluminum halide compositions of this type are known; see U.S. Pat. Nos. 5,157,171 and 5,162,594. In some cases CFC-114a may be employed in the formation of the aluminum halide composition. Thus, in some embodiments, use of sufficient excess of CFC-114a enables the production of $AlCl_xF_{3-x}$ in situ from anhydrous aluminum chloride so that a fluorine-containing catalyst is obtained.

Both CFC-114a and TFE are available commercially or may be prepared by methods known in the art.

The addition reaction involving CFC-114a and TFE is based on a stoichiometry of 1 mole of CFC-114a per mole of TFE. However, an excess of either reactant may be used as desired. An excess of CFC-114a may reduce cycloaddition of TFE with itself. An excess of TFE may promote TFE-based by-products such as the cycloaddition reaction products and/or the formation of five carbon products. Typically, the mole ratio of TFE to CFC-114a is about 1.5 or less (e.g., from about 0.3:1 to about 1.1:1).

In one embodiment, the addition reaction step may be conducted in a continuous manner. In one embodiment, in the continuous mode, a mixture of CFC-114a and TFE may be passed through or over a bed or body of the aluminum halide composition (which may be under agitation) at suitable temperature and pressure to form a product stream, and the desired products (e.g., CFC-318ma) may be recovered from the stream by conventional methods such as fractional distillation.

In another embodiment, the addition reaction may be conducted in a batchwise manner. In one embodiment, in the batch process, the reactants and the aluminum halide composition may be combined in a suitable reactor to form a reaction mixture, and the mixture held at a suitable temperature and pressure (normally under agitation) until a desired degree of conversion is obtained. In one embodiment, the reactor is initially charged with the aluminum halide composition, and optionally with a diluent, then the CFC-114a and TFE are fed in the desired mole ratio (as separate streams or as a combined stream) into the reactor and maintained therein until the reaction is substantially complete. If the reactor is fed with CFC-114a and the aluminum halide composition are fed to the reactor in the substantial absence of the TFE, then the reactor and ingredients should be kept relatively cold (e.g., between about −78° C. and 10° C.) to discourage disproportionation of the CFC-114a to ethanes having different fluorine content.

In one embodiment, the addition reaction may be practiced with a solvent or diluent for the CFC-114a and TFE. Typically, the CFC-114a and TFE are diluted; however, the diluent may be primarily the CFC-318ma produced in the addition reaction. In some embodiments, solvents which may be used include $CH_2Cl_2$, $CHCl_3$, $CCl_4$, $CHCl_2CF_3$, $CClF_2CClF_2$, and cyclo-$C_4Cl_2F_6$ and mixtures thereof.

In one embodiment, the addition reaction zone temperature is typically in the range of from about 0° C. to about 100° C. In another embodiment, the addition reaction zone temperature is in the range of from about 20° C. to about 80° C.

In one embodiment, the reaction pressure may vary widely. In another embodiment, the reaction is carried out at elevated pressures, particularly pressures generated autogenously in conformity with the reaction temperature employed. In certain embodiments, the pressure may be adjusted by controlling the amount of unreacted CFC-114a and TFE.

In one embodiment, at normally employed temperatures, the reaction time is typically between about 0.2 hour and 12 hours.

In one embodiment, the amount of aluminum halide catalyst composition employed is in the range of from about one to about twenty percent by weight based on the weight of the CFC-114a reactant.

In one embodiment, the effluent from the addition reaction zone (continuous or batch) typically includes CFC-318ma, unreacted CFC-114a and/or TFE. It has been found in accordance with this invention that the CFC-318ma isomer can be produced with high selectivity (about 50 mole % or more of three-carbon addition products).

In one embodiment, the reaction products may be recovered from the reaction zone by use of a suitable conventional means such as by filtration and/or distillation. In another embodiment, in batch mode, it is normally convenient to separate the reaction products from the aluminum halide composition and to use the separated aluminum halide composition in subsequent batches.

Further details of the addition reaction, per se, described herein above may be found in U.S. Pat. No. 6,066,768.

In one embodiment, the $CF_3CCl_2CF_2CF_3$(CFC-318ma) produced by the addition reaction as described above can be used to produce $CF_3CCl$=$CFCF_3$ (CFC-1317mx) by catalytic dehalogenation.

In one embodiment the CFC-318ma is separated from the effluent from the addition reaction zone. In another embodiment CFC-318ma that is present in the effluent from the addition reaction zone, is fed directly to a dehalogenation reaction zone to produce CFC-1317mx.

In other embodiments, CFC-318ma may be produced by other processes known in the art including processes disclosed in U.S. Pat. No. 3,215,748; processes disclosed in Petrov et al., *Journal of Fluorine Chemistry* (1998) volume 89, no. 1, pages 125-130; and other known processes.

In one embodiment, the present disclosure provides a process comprising reacting $CF_3CCl_2CF_2CF_3$ (CFC-318ma) with hydrogen in the presence of a dehalogenation catalyst to produce $CF_3CCl$=$CFCF_3$ (CFC-1317mx).

Dehalogenation catalysts containing copper, nickel, chromium, palladium, and ruthenium are known in the art. They may be prepared by either precipitation methods or impregnation methods as generally described by Satterfield on pages 87-112 in *Heterogeneous Catalysis in Industrial Practice*, 2$^{nd}$ edition (McGraw-Hill, New York, 1991).

In one embodiment, the catalyst for the dehalogenation of CFC-318ma to CFC-1317mx is selected from the group consisting of copper on carbon, copper on calcium fluoride, palladium on barium sulfate, palladium/barium chloride on alumina, Lindlar catalyst (palladium on $CaCO_3$, poisoned with lead), copper and nickel on carbon, nickel on carbon, nickel on calcium fluoride, copper/nickel/chromium on calcium fluoride and unsupported alloys of copper and nickel.

In another embodiment, the catalyst is selected from the group consisting of copper on carbon, copper on calcium fluoride, copper and nickel on carbon, nickel on carbon, copper/nickel/chromium on calcium fluoride and unsupported alloys of copper and nickel. In one embodiment, the amount of copper on carbon or calcium fluoride support is from about 1% by weight to about 25% by weight. In one embodiment, the carbon support may be acid washed carbon.

In another embodiment, the catalyst is palladium on barium sulfate catalyst that may contain from about 0.05% to 10% by weight palladium. In another embodiment, copper and nickel on carbon may contain from about 1% to about 25% by weight copper and nickel combined on the carbon support. In certain embodiments, the carbon support may be any of the carbon supports as described previously herein for other catalysts. The weight ratio of the copper to nickel in the copper and nickel on carbon catalyst may range from about 2:1 to about 1:2.

In one embodiment, the palladium/barium chloride on alumina catalyst may contain from about 1% to about 25% by weight barium chloride and from about 0.05% to about 10% by weight palladium relative to the total weight of the catalyst composition. Preparation of a palladium/barium chloride on alumina catalyst is described in U.S. Pat. No. 5,243,103, the disclosure of which is herein incorporated by reference.

In one embodiment, the dehalogenation catalyst may be copper/nickel/chromium on calcium fluoride. In one embodiment, the molar ratio of copper:nickel:chromium oxide in the copper/nickel/chromium on calcium fluoride catalyst is from about 0 to about 1 copper, from about 0.5 to about 3.0 nickel, and from about 0 to about 2 chromium. In one embodiment, the molar ratio of copper:nickel chromium in the copper/nickel/chromium on calcium fluoride catalyst is 1.0:1.0:1.0. In another embodiment, the molar ratio is 1.0:2.0:1.0. In yet another embodiment, the molar ratio is 1.0:2.0:0.25. In yet another embodiment, the molar ratio is 0.5:3.0:0.5. In yet another embodiment, the molar ratio is 0.5:0.5:2.0. In yet another embodiment, the molar ratio is 0:3.0:1.0. In yet another embodiment, the molar ratio is 1:3.0:0. In one embodiment, the weight ratio of total catalyst material to support material may be from about 1:2 to about 2:1. Preparation of the copper/nickel/chrome catalyst is described in U.S. Pat. No. 2,900,423.

In one embodiment, the unsupported alloys of copper and nickel include those described by Boudart in *Journal of Catalysis,* 81, 204-13, 1983, the disclosure of which is herein incorporated by reference. In one embodiment, the mole ratio of Cu:Ni in the catalysts may range from about 1:99 to about 99:1. In another embodiment, the mole ratio of Cu:Ni is about 1:1.

In one embodiment, the dehalogenation reaction zone temperature is typically in the range of from about 200° C. to about 500° C. In another embodiment, the dehalogenation reaction zone temperature is in the range of from about 300° C. to about 450° C.

In one embodiment, the dehalogenation reaction pressure may vary widely. In another embodiment, the reaction is carried out at elevated pressures.

In one embodiment, the molar ratio of hydrogen to organic (CFC-318ma) feed for the dehalogenation reaction ranges from about 0.5:1 to about 25:1. In another embodiment, the molar ratio of hydrogen to organic feed ranges from about 1.5:1 to about 2.5:1.

In one embodiment of the dehalogenation reaction, the contact time for the process ranges from about 10 to about 120 seconds.

According to another aspect of the present invention, there is provided a process comprising reacting $CF_3CCl\!=\!CFCF_3$ (CFC-1317mx) with hydrogen in the presence of a dehalogenation catalyst, thus producing $CF_3C\!\equiv\!CCF_3$ (hexafluoro-2-butyne).

In one embodiment, the CFC-1317mx may be further reacted with more hydrogen to produce hexafluoro-2-butyne ($CF_3C\!\equiv\!CCF_3$). This second dehalogenation reaction may be conducted under the same conditions and with the same catalysts as described above for the first dehalogenation reaction for converting CFC-318ma to CFC-1317mx. In another embodiment, conditions may vary from the previous dehalogenation reaction in order to optimize production of hexafluoro-2-butyne and minimize undesirable by-products.

In one embodiment, the second dehalogenation reaction effluent may comprise hexafluoro-2-butyne, HCl, HF, and in some cases also propylene, hexafluoro-2-butene (HFC-1336), 2-hydroperfluoro-2-butene (HFC-1327), and certain butene isomers.

In one embodiment, the hexafluoro-2-butyne may be reacted further by a hydrogenation reaction to produce 1,1,1,4,4,4-hexafluoro-2-butene. 1,1,1,4,4,4-hexafluoro-2-butene may exist as one of two stereoisomers, E or Z. In one embodiment of the hydrogenation reaction, the E isomer may be the predominant product. In another embodiment of the hydrogenation reaction, the Z isomer may be the predominant product. In yet another embodiment, the product of the hydrogenation reaction to produce 1,1,1,4,4,4-hexafluoro-2-butene from hexafluoro-2-butyne may produce essentially equimolar quantities of each of the E and Z isomers.

As used herein, by predominant isomer is meant that the particular isomer is produced in greater than 50 mole percent. As used herein, by essentially equimolar quantities is meant that each of the E and Z isomer is produced at about 50 mole percent.

In one embodiment, the hydrogenation process comprises reacting hexafluoro-2-butyne, in a pressure vessel, with a hydrogenation catalyst and hydrogen to produce 1,1,1,4,4,4-hexafluoro-2-butene.

In one embodiment, the hydrogenation catalyst may comprise any hydrogenation catalyst known in the art. In another embodiment, the hydrogenation catalyst may comprise any metal hydrogenation catalyst. The metal catalysts may be supported or unsupported. In another embodiment, in particular, the hydrogenation catalyst may be any platinum group metal, including platinum, palladium, rhodium, and ruthenium. In another embodiment, the hydrogenation catalyst may comprise non-precious metal catalysts. In particular, the hydrogenation catalyst may comprise non-precious metal catalysts based on nickel (such as Raney nickel) and combinations of nickel with copper, manganese, zinc, and chromium. In yet another embodiment, the hydrogenation catalyst may comprise a Lindlar catalyst.

A Lindlar catalyst is a heterogeneous palladium catalyst on a calcium carbonate support, which has been deactivated or conditioned with a lead compound. The lead compound can be lead acetate, lead oxide, or any other suitable lead compound. In one embodiment, the catalyst is prepared by reduction of a palladium salt in the presence of a slurry of calcium carbonate, followed by the addition of the lead compound. In one embodiment, the palladium salt in palladium chloride. In another embodiment, the catalyst is deactivated or conditioned with quinoline. The amount of palladium on the support is typically 5% by weight but may be any catalytically effective amount.

In one embodiment, the amount of the catalyst used is from about 0.5% by weight to about 4% by weight of the amount of the hexafluoro-2-butyne. In another embodiment, the amount of the catalyst used is from about 1% by weight to about 3% by weight of the amount of the hexafluoro-2-butyne. In yet another embodiment, the amount of the catalyst used is from about 1% to about 2% by weight of the amount of the fluorinated hexafluoro-2-butyne.

In some embodiments, the hydrogenation reaction is conducted in a solvent. In one such embodiment, the solvent is an alcohol. Typical alcohol solvents include ethanol, i-propanol and n-propanol. In another embodiment, the solvent is a fluorocarbon or hydrofluorocarbon. Typical fluorocarbons or hydrofluorocarbons include 1,1,1,2,2,3,4,5,5,5-decafluoropentane and 1,1,2,2,3,3,4-heptafluorocyclopentane.

In one embodiment, the process is conducted in a batch-wise process.

In another embodiment, the process is conducted in a continuous process in the gas phase.

In one embodiment, reaction of the hexafluoro-2-butyne with hydrogen in the presence of the catalyst may be done with addition of hydrogen in portions, with increases in the pressure of the vessel of no more than about 100 psi with each addition. In another embodiment, the addition of hydrogen is controlled so that the pressure in the vessel increases no more than about 50 psi with each addition. In one embodiment, after enough hydrogen has been consumed in the hydrogenation reaction to convert at least 50% of the hexafluoro-2-butyne to 1,1,1,4,4,4-hexafluoro-2-butene, hydrogen can be added in larger increments for the remainder of the reaction. In another embodiment, after enough hydrogen has been consumed in the hydrogenation reaction to convert at least 60% of the hexafluoro-2-butyne to 1,1,1,4,4,4-hexafluoro-2-butene, hydrogen can be added in larger increments for the remainder of the reaction. In yet another embodiment, after enough hydrogen has been consumed in the hydrogenation reaction to convert at least 70% of the hexafluoro-2-butyne to 1,1,1,4,4,4-hexafluoro-2-butene, hydrogen can be added in larger increments for the remainder of the reaction. In one embodiment, the larger increments of hydrogen addition can be 300 psi. In another embodiment, the larger increments of hydrogen addition can be 400 psi.

In one embodiment, the amount of hydrogen added is about one molar equivalent per mole of hexafluoro-2-butyne. In another embodiment, the amount of hydrogen added is from about 0.9 moles to about 1.3 moles, per mole of hexafluoro-2-butyne. In yet another embodiment, the amount of hydrogen added is from about 0.95 moles to about 1.1 moles, per mole of hexafluoro-2-butyne. In yet another embodiment, the amount of hydrogen added is from about 0.95 moles to about 1.03 moles, per mole of hexafluoro-2-butyne.

In one embodiment, the hydrogenation is performed at ambient temperature. In another embodiment, the hydrogenation is performed at above ambient temperature. In yet another embodiment, the hydrogenation is performed at below ambient temperature. In yet another embodiment, the hydrogenation is performed at a temperature of below about 0° C.

In one embodiment of a continuous process, a mixture of hexafluoro-2-butyne and hydrogen are passed through a reaction zone containing the catalyst. In one embodiment, the molar ratio of hydrogen to hexafluoro-2-butyne is about 1:1. In another embodiment of a continuous process, the molar ratio of hydrogen to hexafluoro-2-butyne is less than 1:1. In yet another embodiment, the molar ratio of hydrogen to hexafluoro-2-butyne is about 0.67:1.0.

In one embodiment of a continuous process, the reaction zone is maintained at ambient temperature. In another embodiment of a continuous process, the reaction zone is maintained at a temperature of 30° C. In yet another embodiment of a continuous process, the reaction zone is maintained at a temperature of about 40° C.

In one embodiment of a continuous process, the flow rate of hexafluoro-2-butyne and hydrogen is maintained so as to provide a residence time in the reaction zone of about 30 seconds. In another embodiment of a continuous process, the flow rate of hexafluoro-2-butyne and hydrogen is maintained so as to provide a residence time in the reaction zone of about 15 seconds. In yet another embodiment of a continuous process, the flow rate of hexafluoro-2-butyne and hydrogen is maintained so as to provide a residence time in the reaction zone of about 7 seconds.

It will be understood, that contact time in the reaction zone is reduced by increasing the flow rate of hexafluoro-2-butyne and hydrogen into the reaction zone. As the flow rate is increased this will increase the amount of hexafluoro-2-butyne being hydrogenated per unit time. Since the hydrogenation is exothermic, depending on the length and diameter of the reaction zone, and its ability to dissipate heat, at higher flow rates it may be desirable to provide a source of external cooling to the reaction zone to maintain a desired temperature.

In one embodiment of a continuous process, the amount of palladium on the support in the Lindlar catalyst is 5% by weight. In another embodiment, the amount of palladium on the support in the Lindlar catalyst is greater than 5% by weight. In yet another embodiment, the amount of palladium on the support can be from about 5% by weight to about 1% by weight.

In one embodiment, upon completion of a batch-wise or continuous hydrogenation process, the 1,1,1,4,4,4-hexafluoro-2-butene can be recovered through any conventional process, including for example, fractional distillation. In another embodiment, upon completion of a batch-wise or continuous hydrogenation process, the 1,1,1,4,4,4-hexafluoro-2-butene is of sufficient purity to not require further purification steps.

EXAMPLES

The concepts described herein will be further described in the following examples, which do not limit the scope of the invention described in the claims.

Example 1

Synthesis of CFC-318ma ($CF_3CCl_2CF_2CF_3$)

A 400 mL Hastelloy® C shaker tube was charged with 6 gm of aluminum chlorofluoride ($AlCl_xF_{3-x}$). The tube was sealed, cooled to −78° C., evacuated, purged with nitrogen three times, and charged with 80 gm (0.468 mole) of $CF_3CCl_2F$ (CFC-114a). The tube was then placed in a barricade and agitated. 10 gm (0.10 mole) of TFE were added and the tube was heated to 60° C. over the course of about 22 min; the pressure rose to 50 psig. An additional 30 gm (0.40 mole total) of TFE were added over the next 0.5 hr; the maximum pressure was 162 psig. The temperature was held at 60° C. for 6 hr; the pressure in the tube gradually increased to 127 psig. Upon opening the tube, 93.2 gm (88% mass recovery) of product were obtained which consisted of a clear liquid over a brown flocculent solid. Analysis of the liquid product by GC and GCMS indicated the products in Table 1. The $^{19}F$ NMR data is consistent with CFC-318ma.

TABLE 1

| Component | Formula | GC Area % |
|---|---|---|
| CFC-318ma | $CF_3CCl_2CF_2CF_3$ | 80.9 |
| CFC-114a | $CF_3CCl_2F$ | 13.5 |
| CFC-113a | $CF_3CCl_3$ | 3.6 |

Example 2

Conversion of CFC-318ma to CFC-1317mx

An Inconel® tube (⅝ inch OD) was filled with 5 cc (6.54 gm) of Ni/Cu/Cr/$CaF_2$ pellets, crushed and sieved to 12/20 mesh. This catalyst may be made by the process described in U.S. Pat. No. 2,900,423. The temperature of the catalyst bed was raised to 350° C. and purged with nitrogen (50 sccm, $8.3 \times 10^{-7}$ m$^3$) for 60 minutes and then with hydrogen for 30 minutes. The temperature was then raised to 425° C. while still purging with $H_2$ for 60 minutes. CFC-318ma was then vaporized at 70° C. and reacted with hydrogen over the above catalyst at the conditions shown in Table 2, to give primarily CFC-1317mx.

TABLE 2

| Temp, °C. | Contact Time, sec | $H_2$/Org. ratio | CFC-1318my | HFC-1327 | HFC-347 | CFC-1215xc | HCFC-1326 | CFC-1317mx |
|---|---|---|---|---|---|---|---|---|
| 350 | 19.5 | 4.1 | 0% | 47% | 1% | 2% | 0% | 49% |
| 350 | 19.5 | 5.0 | 1% | 40% | 1% | 3% | 1% | 51% |
| 395 | 14.7 | 1.5 | 0% | 54% | 1% | 2% | 1% | 37% |
| 401 | 14.7 | 1.5 | 0% | 23% | 0% | 9% | 1% | 60% |
| 400 | 14.7 | 2.0 | 0% | 19% | 0% | 11% | 2% | 60% |
| 400 | 14.6 | 2.5 | 0% | 17% | 0% | 11% | 3% | 61% |

Example 3

Conversion of CFC-1317mx to hexafluoro-2-butyne

Using the same catalyst described in Example 2 and the same technique, CFC-1317mx can be reacted with hydrogen to make hexafluoro-2-butyne as shown in Table 3.

TABLE 3

| Temp, °C. | Contact time, sec | $H_2$/Org ratio | Mole Percents | | | | | |
|---|---|---|---|---|---|---|---|---|
| | | | $CF_3C\equiv CCF_3$ | HFC-1336 | propylene | CFC-1317 | HFC-1327 | butene |
| 383 | 16.0 | 1.8 | 11.4% | 3.3% | 1.45% | 48.18% | 18.11% | 0.91% |
| 401 | 16.0 | 1.8 | 17.7% | 1.7% | 1.17% | 46.65% | 13.63% | 0.97% |
| 400 | 15.9 | 2.2 | 19.2% | 0.0% | 0.91% | 51.10% | 12.20% | 0.88% |
| 399 | 15.9 | 2.2 | 17.8% | 0.0% | 0.84% | 54.88% | 10.27% | 0.93% |
| 400 | 15.9 | 2.7 | 16.2% | 0.0% | 0.66% | 60.68% | 7.71% | 0.80% |

HFC-1336 = hexafluoro-2-butene
CFC-1317 = 2-chloro-perfluoro-2-butene
HFC-1327 = 2-hydro-perfluoro-2-butene
Butene = butene (isomer unknown)

Example 4

Example 4 demonstrates the selective hydrogenation of hexafluoro-2-butyne to produce a mixture of cis- and trans-1,1,1,4,4,4-hexafluoro-2-butene.

5 g of Lindlar catalyst (5% Pd on $CaCO_3$ poisoned with lead) was charged in 1.3 L rocker bomb. 480 g (2.96 mole) of hexafluoro-2-butyne was charged in the rocker. The reactor was cooled down (−78° C.) and evacuated. After the bomb was warmed up to room temperature, $H_2$ was added slowly, by increments which did not exceed Δp=50 psi. A total of 3 moles $H_2$ were added to the reactor. A gas chromatographic analysis of the crude product indicated the mixture consisted of $CF_3C\equiv CCF_3$ (0.236%), trans-isomer of $CF_3CH=CHCF_3$ (0.444%), saturated $CF_3CH_2CH_2CF_3$ (1.9%) $CF_2=CHCl$, impurity from starting butyne, (0.628%), cis-isomer of $CF_3CH=CHCF_3$ (96.748%). Distillation afforded 287 g (59% yield) of 100% pure cis-$CF_3CH=CHCF_3$ (boiling point 33.3° C.). MS: 164 [MI], 145 [M-19], 95 [$CF_3CH=CH$], 69 [$CF_3$]. NMR $H^1$: 6.12 ppm (multiplet), $F^{19}$: −60.9 ppm (triplet J=0.86 Hz).

Example 5

Example 5 demonstrates the hydrogenation of hexafluoro-2-butyne with 2% catalyst by weight to produce predominantly cis-1,1,1,4,4,4-hexafluoro-2-butene.

Into a 1.3 L Hastelloy® reactor 10 g of Lindlar catalyst was loaded. Then, hexafluoro-2-butyne 500 g (3.08 mole) was added to the reactor. Hydrogen was added by small increments of 50-100 psi. A total of 1100 psi of hydrogen was added in total. Hydrogen was consumed at the rate of 150 psi/hr average during 6.5 hrs. Analysis of the product by gas chromatography indicated that 93.7% of hexafluorobutyne was converted into cis-$CF_3CH=CHCF_3$, with 4.8% of saturated $CF_3CH_2CH_2CF_3$.

Example 6

Example 6 demonstrates the hydrogenation of hexafluoro-2-butyne with 1% catalyst by weight to produce predominantly cis-1,1,1,4,4,4-hexafluoro-2-butene.

Into a 1.3 L Hastelloy® reactor 5 g of Lindlar catalyst was loaded. Then, hexafluoro-2-butyne 500 g (3.08 mole) was added to the reactor. Hydrogen was added by small increments of 30-50 psi. 1414 psi was added total (4.0 moles hydrogen). Hydrogen was consumed at the rate of 50 psi/hr average during 28 hours. Analysis of the resulting product mixture indicated 80.7% cis-$CF_3CH=CHCF_3$, and 19.3% saturated $CF_3CH_2CH_2CF_3$.

Example 7

Example 7 demonstrates the hydrogenation of hexafluoro-2-butyne in a continuous process to produce a mixture of cis- and trans-1,1,1,4,4,4-hexafluoro-2-butene.

A Hastelloy® tube reactor 10" long with a 5" O.D. (outside diameter) and 0.35" wall thickness was filled with 10 g of Lindlar catalyst. The catalyst was conditioned at 70° C. with a flow of hydrogen for 24 hours. Then a flow of a 1:1 mole ratio of hexafluoro-2-butyne and hydrogen was passed through the reactor at 30° C. at a flow rate sufficient to provide a 30 second contact time. The product mixture was collected in a cold trap after exiting the reactor and analyzed by gas chromatography. The product mixture was found to contain $CF_3CH=CHCF_3$ (cis) (72%), $CF_3CH=CHCF_3$ (trans) (8.8%), $CF_3CH_2CH_2CF_3$ (7.8%) and $CF_3C\equiv CCF_3$ (3.3%).

Example 8

Example 8 demonstrates the hydrogenation of hexafluoro-2-butyne in a continuous process with a 15 second contact time to produce a mixture of cis- and trans-1,1,1,4,4,4-hexafluoro-2-butene.

The procedure of Example 7 was followed, with the exception that the flow rate was adjusted to provide a contact time of 15 seconds. The reaction was slightly exothermic, with the reactor warming to 35-36° C. Analysis of the product mixture indicated $CF_3CH=CHCF_3$ (cis) (72%), $CF_3CH=CHCF_3$ (trans) (9.3%), $CF_3CH_2CH_2CF_3$ (11.3%) and $CF_3C\equiv CCF_3$ (3.9%).

Example 9

Example 9 demonstrates the hydrogenation of hexafluoro-2-butyne in a continuous process with a hydrogen:alkyne mole ratio of 0.67:1 to produce a mixture of cis- and trans-1,1,1,4,4,4-hexafluoro-2-butene.

The procedure of example 7 was followed, with the exception that the mole ratio of hydrogen:hexafluoro-2-butyne fed to the reactor was 0.67:1.0. Analysis of the product mixture indicated $CF_3CH=CHCF_3$ (cis) (65.3%), $CF_3CH=CHCF_3$ (trans) (4.4%), $CF_3CH_2CH_2CF_3$ (3.4%) and $CF_3C\equiv CCF_3$ (23.5%).

Example 10

Example 10 demonstrates the hydrogenation of hexafluoro-2-butyne in a continuous process with a 7 second contact time to produce a mixture of cis- and trans-1,1,1,4,4,4-hexafluoro-2-butene.

The procedure of example 7 was followed, with the exception that the flow rate was adjusted to provide a contact time of 7 seconds. The reaction was slightly exothermic, with the reactor warming to 42° C. Analysis of the product mixture indicated $CF_3CH=CHCF_3$ (cis) (72.5%), $CF_3CH=CHCF_3$ (trans) (8.7%), $CF_3CH_2CH_2CF_3$ (8.6%) and $CF_3C\equiv CCF_3$ (6.9%).

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

What is claimed is:

1. A process comprising:
   reacting $CF_3CCl=CFCF_3$ (CFC-1317mx) with hydrogen in the presence of a dehalogenation catalyst to produce $CF_3CECCF_3$ (hexafluoro-2-butyne), wherein said dehalogenation catalyst comprises copper/nickel/chromium on calcium fluoride or an unsupported alloy of copper and nickel.

2. The process of claim 1 further comprising:
   reacting $CF_3CECCF_3$, in a pressure vessel, with a hydrogenation catalyst and hydrogen to produce $CF_3CH=CHCF_3$ (1,1,1,4,4,4-hexafluoro-2-butene).

3. The process of claim 2 wherein said hydrogenation catalyst comprises a Lindlar catalyst.

4. The process of claim 1, wherein said dehalogenation catalyst comprises copper/nickel/chromium on calcium fluoride with a molar ratio of copper:nickel:chromium from about 0 to 1 copper, from about 0.5 to 3.0 nickel, and from about 0 to 2 chromium.

5. The process of claim 2, wherein the hydrogenation reaction is conducted in a continuous process in the gas phase.

6. The process of claim 1 wherein the molar ratio of hydrogen to $CF_3CCl_2CF_2CF_3$ (CFC-318ma) feed for the dehalogenation reaction ranges from about 0.5:1 to 25:1.

7. The process of claim 1 wherein the $CF_3CCl=CFCF_3$ (CFC-1317mx) is produced by reacting $CF_3CCl_2CF_2CF_3$ (CFC-318ma) with hydrogen in the presence of a dehalogenation catalyst.

8. The process of claim 7, wherein the $CF_3CCl_2CF_2CF_3$ (CFC-318ma) is produced by an addition reaction of $CF_3CCl_2F$ (CFC-114a) and $CF_2=CF_2$ (tetrafluoroethylene) in the presence of a catalyst.

9. The process of claim 8, wherein the catalyst is an aluminum halide catalyst.

* * * * *